(12) United States Patent
Dobson

(10) Patent No.: US 10,884,502 B2
(45) Date of Patent: Jan. 5, 2021

(54) PROVIDING MEDIATED SOCIAL INTERACTIONS

(71) Applicant: Google LLC, Mountain View, CA (US)

(72) Inventor: Kelly Elizabeth Dobson, Mountain View, CA (US)

(73) Assignee: Google LLC, Mountain View, CA (US)

(*) Notice: Subject to any disclaimer, the term of this patent is extended or adjusted under 35 U.S.C. 154(b) by 0 days.

(21) Appl. No.: 16/463,629

(22) PCT Filed: Nov. 21, 2017

(86) PCT No.: PCT/US2017/062665
§ 371 (c)(1),
(2) Date: May 23, 2019

(87) PCT Pub. No.: WO2018/098098
PCT Pub. Date: May 31, 2018

(65) Prior Publication Data
US 2019/0317605 A1 Oct. 17, 2019

Related U.S. Application Data

(60) Provisional application No. 62/425,737, filed on Nov. 23, 2016.

(51) Int. Cl.
*G06F 3/01* (2006.01)
*G06N 20/00* (2019.01)
(Continued)

(52) U.S. Cl.
CPC ............ *G06F 3/016* (2013.01); *G06F 3/012* (2013.01); *G06F 3/015* (2013.01);
(Continued)

(58) Field of Classification Search
CPC .......... G06F 3/016; G06F 3/015; G06F 3/012; G06F 3/017; G06F 3/00; G06N 20/00
(Continued)

(56) References Cited

U.S. PATENT DOCUMENTS 7,647,560 B2 * 1/2010 Macauley ............... A63F 13/12
715/758
7,835,729 B2 * 11/2010 Hyon ................ H04M 1/72544
455/414.1
(Continued)

FOREIGN PATENT DOCUMENTS

WO   WO 2010120945   10/2010

OTHER PUBLICATIONS

Search Report and Written Opinion received in PCT/US2017/062665, dated May 9, 2018, 4 pages.
(Continued)

*Primary Examiner* — Eric Blount
(74) *Attorney, Agent, or Firm* — Dority & Manning, PA

(57) ABSTRACT

Systems and methods of providing mediated social interactions are provided. For instance, a user input from a first user indicative of a request to facilitate a provision of emotive contextual signals to a second user can be received. One or more emotive contextual signals to be provided to the second user can be determined based at least in part on the user input. The one or more emotive contextual signals can include one or more haptic feedback signals intended to facilitate a mediated social interaction associated with the second user.

18 Claims, 4 Drawing Sheets

(51) Int. Cl.
*G06F 3/0488* (2013.01)
*G06Q 50/00* (2012.01)

(52) U.S. Cl.
CPC ......... *G06F 3/04883* (2013.01); *G06N 20/00* (2019.01); *G06Q 50/01* (2013.01)

(58) Field of Classification Search
USPC ........................................ 340/407.1, 407.2
See application file for complete search history.

(56) References Cited

U.S. PATENT DOCUMENTS

| | | | |
|---|---|---|---|
| 7,937,285 B2 | 5/2011 | Goldberg et al. | |
| 8,140,143 B2 | 3/2012 | Picard et al. | |
| 8,545,228 B2 | 10/2013 | Dobson | |
| 8,638,301 B2 * | 1/2014 | Birnbaum | H04M 1/72544 345/173 |
| 9,368,006 B1 * | 6/2016 | Gorilovsky | G08B 6/00 |
| 9,792,602 B2 * | 10/2017 | Eun | H04N 7/14 |
| 9,841,816 B2 * | 12/2017 | Cruz-Hernandez | A61B 5/02438 |
| 9,934,697 B2 * | 4/2018 | O'Dowd | G06F 3/011 |
| 10,065,074 B1 * | 9/2018 | Hoang | G16H 40/63 |
| 10,386,996 B2 * | 8/2019 | Santossio | G06F 3/017 |
| 10,410,180 B2 * | 9/2019 | Druck | G06F 3/04883 |
| 2003/0110450 A1 * | 6/2003 | Sakai | G06F 40/169 715/256 |
| 2007/0149282 A1 * | 6/2007 | Lu | A63F 13/06 463/36 |
| 2008/0027984 A1 * | 1/2008 | Perdomo | G06Q 10/107 |
| 2008/0218490 A1 * | 9/2008 | Kim | G06F 3/0488 345/173 |
| 2009/0131165 A1 * | 5/2009 | Buchner | A63F 13/02 463/30 |
| 2010/0123724 A1 * | 5/2010 | Moore | G06F 3/04817 345/473 |
| 2010/0146407 A1 * | 6/2010 | Bokor | G06F 3/0481 715/757 |
| 2013/0063256 A1 * | 3/2013 | Tartz | G06F 3/005 340/407.1 |
| 2017/0109651 A1 * | 4/2017 | Bruno | G06F 40/30 |
| 2017/0337476 A1 * | 11/2017 | Gordon | G06F 3/011 |
| 2017/0351330 A1 * | 12/2017 | Gordon | G06F 1/163 |
| 2018/0246578 A1 * | 8/2018 | Lenz | A63F 13/212 |

OTHER PUBLICATIONS

Haans, et al. "Mediated Social Touch: A Review of Current Research and Future Directions", Virtual Reality, Jan. 9, 2006, pp. 149-159.

* cited by examiner

PROVIDING MEDIATED SOCIAL INTERACTIONS

PRIORITY CLAIM

The present application is based upon and claims the right of priority under 35 U.S.C. § 371 to International Application No. PCT/US2017/062665, filed on Nov. 21, 2017, which claims the benefit of U.S. Provisional Application Ser. No. 62/425,737 filed Nov. 23, 2016. Applicant claims priority to and the benefit of each of such applications and incorporate all such applications herein by reference in its entirety.

FIELD

The present disclosure relates generally to providing mediated social interactions by one or more computing devices.

BACKGROUND

Humans use their sense of touch to interact with their environments. Such sense of touch can provide useful information regarding spatial aspects of the environment. For instance, the sense of touch can provide information relating to the position and movement of a person's body in space. As another example, the sense of touch can provide information relating to the size, weight, shape, texture, etc. of external object. The sense of touch is particularly useful in social interactions. Contact with another human can evoke strong positive and negative emotional experiences. Human touch can facilitate personal and intimate interpersonal interaction, and can evoke a sense of proximity and connectedness between humans.

Human touch can be simulated using mediated social interaction techniques, wherein various forms of human contact are simulated, for instance, via human-computer interaction systems, teleoperation systems, sensory substitution systems, and other suitable systems. Such systems can allow users to viscerally experience such simulated human contact through the application of various signals to the users. In this manner, mediated social interaction systems can evoke various emotional or biometric responses associated with human contact in the users.

SUMMARY

Aspects and advantages of embodiments of the present disclosure will be set forth in part in the following description, or may be learned from the description, or may be learned through practice of the embodiments.

One example aspect of the present disclosure is directed to a computer-implemented method of providing emotive contextual signals to a user. The method includes receiving, by a first computing device, a user input from a first user indicative of a request to facilitate a provision of emotive contextual signals to a second user. The method further includes determining, by a second computing device, one or more emotive contextual signals to be provided to the second user based at least in part on the user input, the one or more first emotive contextual signals comprising one or more first haptic feedback signals. The first haptic feedback signals may, for example, facilitate or be intended to facilitate a mediated social interaction associated with the second user.

Other example aspects of the present disclosure are directed to systems, apparatus, tangible, non-transitory computer-readable media, user interfaces, memory devices, and electronic devices for providing emotive contextual signals.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
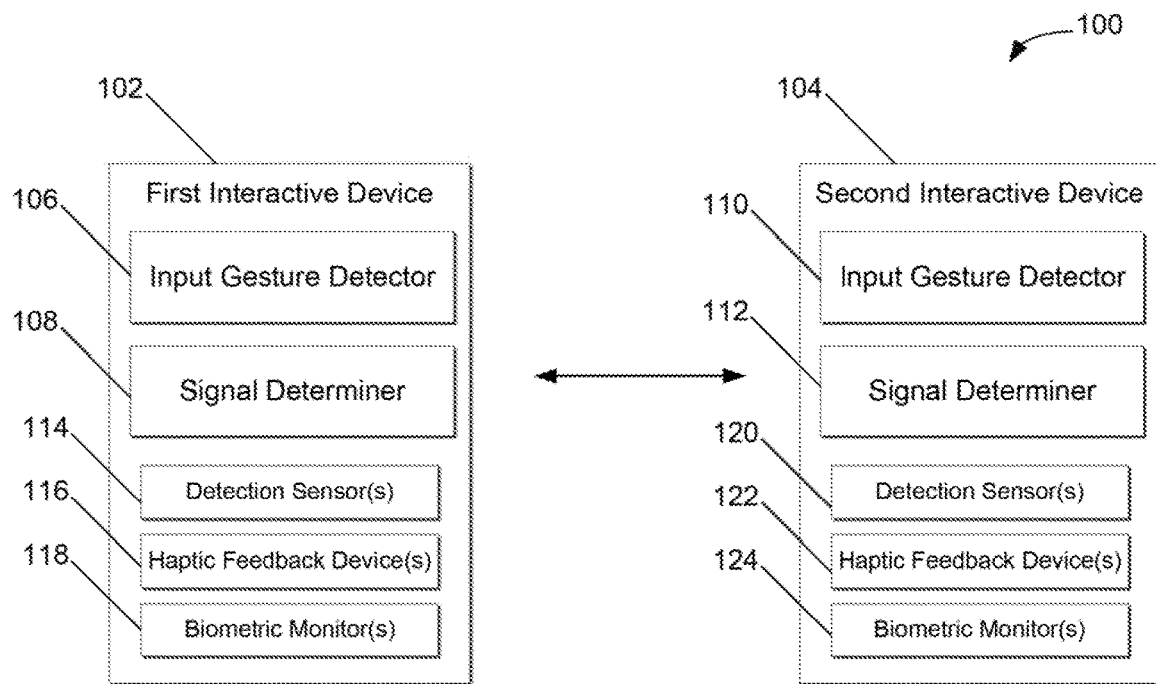
FIG. 1 depicts an example system for providing emotive contextual signals according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to providing emotive contextual signals to a user. For instance, a first user can interact with a first interactive device to facilitate a provision of a mediated social interaction with a second user of a second interactive device. For instance, the mediated social interaction can be a mediated physical interaction. Such mediated interaction can be intended to simulate a physical action performed with respect to the second user and/or to evoke a desired emotional response by the second user. The first user can perform an input gesture or other physical interaction with respect to the first interactive device. One or more emotive contextual signals can be determined based at least in part on the interaction with the first interactive device by the first user. The one or more emotive contextual signals can be, for instance, haptic feedback signals that, when provided to the second user, are intended to simulate an action performed with respect to the second user and/or to evoke an emotional response by the second user. In this manner, the one or more emotive contextual signals can be provided to the second user by the second interactive device with the object of simulating the desired action and/or evoking the desired emotional response associated with the interaction by the first user with the first interactive device.

As used herein, the term "input gesture" can refer to any suitable interaction between a user and an associated interactive device that facilitates a provision of emotive contextual signals to a different user of an interactive device. For instance, the input gesture can be a particular movement pattern of a hand or other input object associated with the user performed proximate the first interactive device (e.g. motion gesture), an actuation of the first interactive device by the user (e.g. actuation of an input device associated with the interactive device), a particular movement or movement pattern of the first interactive device by the user (e.g. moving the interactive device in a particular manner), a touch gesture performed on a surface of the first interactive device, an application of pressure to one or more areas of the interactive device, and/or other suitable interaction. In some implementations, the input gesture performed by the first user can be associated with a particular emotional response that the first user desires to evoke in the second user. In some implementations, the input gesture can be associated with a particular simulated action or behavior that the first user desires to be performed on the second user.

The first and second interactive devices can be any suitable computing device capable of detecting an input gesture and/or providing emotive contextual signals to a user in accordance with example embodiments of the present disclosure. For instance, the interactive devices can each be a general purpose computer, special purpose computer, laptop, desktop, mobile device, navigation system, smartphone, tablet, wearable computing device (e.g. smart garment in accordance with example aspects of the present disclosure, fitness band, smart watch, etc.), a display with one or more processors, or other suitable computing device. In this regard, the first and second interactive devices can include one or more gesture detection sensors. The one or more gesture detection sensors can be configured to detect a suitable input gesture performed by a user with respect to the interactive device. For instance, the one or more gesture detection sensors can include pressure sensors, accelerometers, gyroscopes, magnetometers, inertial measurement units, radar devices, imaging devices, and/or other suitable gesture detection sensors. The first and second interactive devices can further include one or more haptic feedback devices configured to provide emotive contextual signals to a user of the interactive devices. For instance, the one or more haptic feedback devices can include one or more actuators (e.g. vibrotactile actuators, electrotactile actuators, piezoelectric actuators, electromechanical actuators, linear actuators, linear resonant actuators, etc.), motors (e.g. eccentric rotating mass motor, etc.), transducers (e.g. vibrotactile transducers), and/or other suitable haptic feedback device. In this manner, the haptic feedback devices can be configured to provide physical stimuli to the user.

In some implementations, an interactive device in accordance with example aspects of the present disclosure can be implemented within, or otherwise associated with a smart garment that is configured to be worn by the user. For instance, the smart garment can be constructed with a plurality of electrically conductive yarns, as described in greater detail below. Such electrically conductive yarns can be electrically coupled to one or more suitable computing devices and can form one or more circuits configured to implement example aspects of the present disclosure.

According to example aspects of the present disclosure, a user of a first interactive device can interact with the first interactive device by performing an input gesture with respect to the first interactive device. A detection of the performance of the input gesture can facilitate a provision of one or more emotive contextual signals to a user of a second interactive device by the second interactive device. The input gesture can be mapped to a particular emotional response or simulated behavior. The simulated action and/or emotional response can be associated with a mediated social touch performed on the second user by the second interactive device. For instance, a first input gesture can be mapped to an evocation of a soothing feeling, and a second interaction can be mapped to an action that simulates a particular type of touch, such as holding hands. In some implementations, the input gesture mapping can be defined by a predefined gesture mapping scheme that respectively maps a plurality of input gestures to a plurality of emotional responses and/or simulated actions.

In this manner, in response to a detection of a performance of an input gesture by the first user, one or more emotive contextual signals can be determined based on the performed input gesture. For instance, the emotive contextual signals can be determined such that, when provided to the second user, the second user experiences the desired mediated interaction associated with the detected input gesture. For instance, such emotive contextual signals can be haptic feedback signals applied to the second user by the second interactive device. Such haptic feedback signals can be associated with various suitable physical stimuli, such as applied pressure, vibration, temperature, etc. In some implementations, the haptic feedback signals can be an application of an electrical current to the skin of the second user. As indicated, the emotive contextual signals can be determined based at least in part on the mediated social interaction associated with the detected input gesture. In this manner, the emotive contextual signals can be applied to the user to evoke the intended emotional response and/or to simulate the intended action with respect to the second user.

In some implementations, a mediated social interaction can be explicitly mapped to one or more particular emotive contextual signals, such that a particular input gesture facilitates a provision of such particular emotive contextual signals. In this manner, a detection of an input gesture performed by a first user can facilitate a provision of one or more specific emotive contextual signals to a second user. In some implementations, the emotive contextual signals can be determined based at least in part on one or more characteristics of the second user. For instance, one or more biometric signals associated with the second user can be monitored. The emotive contextual signals can be determined based at least in part on the biometric signals. For instance, the biometric signals can include one or more of a heart rate of the second user, a temperature of the second user, a skin conductance of the second user, and/or other suitable biometric signal. In this manner, the emotive contextual signals can be personalized for the second user based at least in part on the biometric characteristics of the second user.

In some implementations, the emotive contextual signals provided to the second user can be adjusted based at least in part on the biometric signals of the second user. For instance, the biometric signals can be monitored in response to a provision of the emotive contextual signals to determine if the provision of the emotive contextual signals is having the desired effect on the second user. For instance, the monitored biometric signals can be compared to target biometric signals associated with the simulated action and/or the emotional response associated with the emotive contextual signals. As another example a biometric response (e.g. a change in biometric signals in response to a reception of the emotive contextual signals) can be compared to a target biometric response associated with the simulated action and/or the emotional response associated with the emotive contextual signals. In this manner, if the user reacts to the emotive contextual signals in a manner inconsistent with the aim of the emotive contextual signals, the emotive contextual signals can be adjusted to facilitate the desired result.

In some implementations, the emotive contextual signals can be determined using one or more machine learning techniques. For instance, data associated with a response of a user to a reception of emotive contextual signals can be used by a suitable machine learning model to "learn" personalized emotive contextual signals that evoke the desired response in the user. Any suitable machine learning model can be used, such as neural networks (e.g., deep neural networks) or other multi-layer non-linear models. Neural networks can include recurrent neural networks (e.g., long short-term memory recurrent neural networks), feed-forward neural networks, or other forms of neural networks. For instance, the machine learning model can receive as input the target emotional response and/or simulated action, and the machine learning model can provide as output the emotive contextual signals to be provided to the user. The machine learning model can be trained using suitable training data to adjust the model based, for instance, on the biometric characteristics of the second user. For instance, the biometric signals and/or biometric response of the user subsequent to a provision of the emotive contextual signals can be compared against target biometric signals and/or biometric response associated with the emotive contextual signals. The machine learning model can be adjusted based at least in part on the comparison. In this manner, the machine learning techniques can be used to personalize the emotive contextual signals towards the second user.

In this manner, the first and second interactive devices can be used respectively by the first and second users to facilitate a mediated social interaction between the users. For instance, the first user and the second user can each use their respective interactive devices to send and receive emotive contextual signals to the other user. Such mediated social interaction can allow the users to use their senses of touch in the interaction via the interactive devices. Such mediated interactions can help to establish a sense of connectedness between the users, and/or to provide various psychological benefits that accompany physical interactions (e.g. direct contact) between humans, such as a sense of intimacy, recovery from stress, calming sensations, and/or other suitable emotional responses. In this manner, the provisions of the emotive contextual signals can simulate such physical interactions.

With reference now to the figures, example aspects of the present disclosure will be discussed in greater detail. For instance, FIG. 1 depicts an example system (100) for providing emotive contextual signals according to example embodiments of the present disclosure. System 100 includes a first interactive device 102 and a second interactive device 104. The first interactive device 102 includes an input gesture detector 106 and a signal determiner 108. Similarly, the second interactive device includes an input gesture detector 110 and a signal determiner 112. The first interactive device 102 can be associated with a first user and the second interactive device 104 can be associated with a second user. The first and second users can respectively use the first and second interactive devices 102 and 104 to facilitate mediated social interactions between the users. In this manner, the first user can perform an input gesture with respect to the first interactive device 102. The input gesture detector can be configured to detect the performance of the input gesture, for instance, using one or more detection sensors 114. The input gesture can be any suitable input gesture, such as a touch gesture performed on a surface of the first interactive device 102, an application of pressure to the first interactive device 102, a causation of movement of the first interactive device 102 in a predefined manner (e.g. shaking, rotating, etc. the first interactive device 102), a motion gesture performed proximate the first interactive device 102 (e.g. an in-air hand gesture, and/or an in-air gesture performed with an input object such as a stylus), or any other suitable input gesture.

The detection sensor(s) 114 can be implemented within or otherwise associated with the first interactive device, and can include any suitable sensors or other gesture detection devices configured to detect a performance of a suitable input gesture. For instance, the detection sensor(s) can include one or more pressure sensors (e.g. capacitive pressure sensors, piezoresistive pressure sensors, electromagnetic pressure sensors, optical pressure sensors, potentiometric pressure sensors, piezoelectric pressure sensors, etc.), position sensors (e.g. accelerometers, gyroscopes, inertial measurement units, etc.), imaging sensors (e.g. optical imaging sensors, radar imaging sensors, LIDAR imaging sensors, etc.), and/or other suitable devices.

The input gesture can be associated with a mediated social interaction to be established between the first and the second user. Such association can be defined by a predefined gesture mapping scheme that respectively corresponds a plurality of suitable input gestures to a plurality of suitable mediated social interactions. For instance, the mediated social interaction can be a mediated physical interaction (e.g. a particular mediated social touch), such as a simulation of holding hands, a simulation of a body hug, a simulation of any other suitable form of physical interaction between humans. In this manner, the mediated social interaction can be associated with an application of any suitable emotive contextual signals intended to simulate the particular mediated social touch on the first or second user. In some implementations, rather than a particular form of touch, the mediated social interaction can be an evocation of a particular emotional response. In this manner, the mediated social interaction can be associated with an application of any suitable emotive contextual signals intended to evoke such particular emotional response in the first or second user.

In some implementations, data indicative of the detected input gesture can be provided to the second interactive device 104. As will be described in more detail with regard to FIG. 2, the communication between the first interactive device 102 and the second interactive device 104 can be implemented by way of one or more networks and one or more relaying devices. Upon receipt of the data indicative of the detected input gesture, the second interactive device 104 can determine one or more emotive contextual signals to be provided to the second user based at least in part on the detected input gesture. For instance, the signal determiner 112 can access the predefined gesture mapping scheme to determine the mediated social interaction associated with the user input. In this manner, the signal determiner 112 can determine the mediated social interaction that the first user desires to establish between the first and second user.

Upon a determination of the mediated social interaction, the signal determiner 112 can determine one or more emotive contextual signals to be provided to the second user. The one or more emotive contextual signals can be any suitable signal that implements the specified mediated social interaction. For instance, the emotive contextual signals can be haptic feedback signals that can be provided to the user via one or more haptic feedback devices 122. For instance, the haptic feedback devices 122 can include one or more actuators (e.g. vibrotactile actuators, electrotactile actuators, piezoelectric actuators, electromechanical actuators, linear actuators, linear resonant actuators, etc.), motors (e.g. eccentric rotating mass motor, etc.), transducers (e.g. vibrotactile transducers), and/or other suitable haptic feedback device. In this regard, the haptic feedback signals can include vibration, pressure, temperature (e.g. heat or warmth), electrical currents, forces, stress, strain, impacts, and/or other suitable forms of haptic feedback or physical stimulations. More particularly, the emotive contextual signals can be haptic feedback signals having varying parameters (e.g. magnitudes, frequencies, etc.). For instance, an emotive contextual signal can be an application of a particular amount of pressure, or a vibration having a particular frequency and/or magnitude.

The emotive contextual signals can be determined based at least in part on the specified mediated social interaction. For instance, in some implementations, the emotive contextual signals can be universal or default emotive contextual signals that correspond to specified mediated social interaction. In this manner, each mediated social interaction specified within the gesture mapping scheme can be further mapped to one or more emotive contextual signals intended to simulate the mediated social interaction. In some implementations, the emotive contextual signals can be personalized for the second user. For instance, the emotive contextual signals intended to simulate the mediated social interaction can be determined based at least in part on one or more biometric characteristics of the second user. In this manner, one or more biometric monitors 122 can be configured to monitor one or more biometric signals of the second user. The biometric monitor(s) can be any suitable devices configured to determine such biometric signals. For instance, the biometric monitor(s) 122 can be configured to monitor a heart rate of the second user, a temperature of the second user, a skin conductance of the second user, etc.

In this manner, the signal determiner 112 can determine the one or more emotive contextual signals by taking into account the biometric characteristics of the second user. For instance, the biometric characteristics of the second user can be used to tailor the emotive contextual signals to the user. In this manner, the emotive contextual signals determined for a particular mediated social interaction for a particular user can depend on the biometric characteristics of the user. In some implementations, the signal determiner 112 can determine the one or more emotive contextual signals to evoke a particular biometric response in the user. For instance, the emotive contextual signals can be determined such that an application of the emotive contextual signals to the second user is intended to lower the second user's heart rate. In some implementations, the personalized emotive contextual signals can be determined by adjusting the default or universal emotive contextual signals associated with a particular mediated social interaction based on the monitored biometric signals of the second user.

Upon a determination of the emotive contextual signals, the emotive contextual signals can be provided to the second user via the haptic feedback device(s) 122. As indicated, the emotive contextual signals can be haptic feedback signals, such as vibration, pressure, temperature (e.g. heat or warmth), electrical currents, forces, stress, strain, impacts, and/or other suitable forms of haptic feedback or physical stimulations. The haptic feedback devices may provide such signals to the second user, for instance, while the second user is making contact with the second interactive device 104.

Various users may react differently to a reception of various emotive contextual signals. In this manner, in some implementations, the biometric monitor(s) 124 can continue to monitor the biometric signals of the second user during the application of the emotive contextual signals and/or subsequent to the application of the emotive contextual signals. In such implementations, the second interactive device 104 can use such monitored signals to determine if the emotive contextual signals are having the desired effect on the second user. For instance, the monitored biometric signals can be compared to target biometric signals associated with the mediated social interaction to determine if the emotive contextual signals are having the desired effect. In some implementations, the biometric reaction (e.g. change in heart rate, body temperature, etc.) of the user can be compared to a target biometric reaction or target emotional response. If the biometric reaction of the user does not match the target biometric reaction, the emotive contextual signals can be adjusted to attempt to evoke the target biometric reaction.

In some implementations, the biometric reactions of a user to a provision of various emotive contextual signals can be tracked over time to learn the preferences and characteristics of the user. For instance, example aspects of the present disclosure can include learning how such user reacts to various emotive contextual signals. The learned reactions can be used to determine personalized emotive contextual signals to be provided to the user to facilitate various mediated social interactions. For instance, the emotive contextual signals provided to the user to facilitate various mediated social interactions can be adjusted over time based on the reaction of the user to the provision of such emotive contextual signals. The adjustments can be made to more accurately facilitate the mediated social interactions between users. In some implementations, such adjustments can be made using one or more machine learning techniques. For instance, a machine learning model (e.g. neural network or other model) can be used to learn the user's preferences and to determine the personalized emotive contextual signals.

In this manner, the first interactive device 102 and the second interactive device 104 can be used by the first user and the second user to facilitate mediated social interactions between the first and second users. Although the above examples described the first user facilitating a provision of emotive contextual signals to the second user, it will be appreciated that the second user may also use the second interactive device 104 to facilitate a provision of emotive contextual signals to the first user. For instance, the second user may perform an input gesture, and the input gesture detector 110 can detect such performance of the input gesture using one or more detection sensors 120. Similar to the detection sensor(s) 114, the detection sensor(s) 120 can include one or more pressure sensors, position sensors, imaging sensors, etc. The signal determiner 108 of the first interactive device 102 can determine one or more emotive contextual signals based at least in part on the input gesture detected by the input gesture detector 110. The emotive contextual signals can be provided to the first user via one or more haptic feedback devices 116. Similar to the haptic feedback device(s) 122 of the second interactive device 104, the haptic feedback device(s) 116 can include one or more actuators, motors, vibration engines, temperature applicators, etc. configured to apply haptic feedback signals to the first user. In some implementations, the emotive contextual signals can be determined based at least in part on one or more biometric characteristics of the first user monitored by one or more biometric monitors 118.

The first interactive device 102 and the second interactive device 104 can be any suitable computing devices capable of detecting an input gesture and/or providing emotive contextual signals to a user in accordance with example embodiments of the present disclosure. For instance, the interactive devices can each be a general purpose computer, special purpose computer, laptop, desktop, mobile device, navigation system, smartphone, tablet, wearable computing device, a display with one or more processors, or other suitable computing device. More particularly, the interactive devices 102, 104 can be devices capable of applying suitable emotive contextual signals to a user while in physical contact with a user. The interactive devices can be configured such that a user can grip, hold, wear, press up against, etc. at least a portion of the interactive device to receive the emotive contextual signals provided by the interactive device. In this manner, the form factor of the interactive device can be designed to facilitate such provision of emotive contextual signals.

In some implementations, the interactive device 102 and/or the interactive device 104 can be smart garments constructed using electrically conductive yarns. Fabric structures, such as garments, made in accordance with the present disclosure are generally formed from yarns that are woven or knitted together. In one embodiment, at least certain of the yarns are electrically conductive. The electrically conductive yarns can be woven into the fabric structure in order to form various different electronic circuits. Various different types of electrical devices can be attached to the yarns and controlled by a controller, such as a microprocessor. In one embodiment, the entire fabric structure can be made from electrically conductive yarns. In an alternative embodiment, however, the fabric structure can be a combination of conductive yarns and non-conductive yarns. When combining conductive yarns and non-conductive yarns, a fabric can be produced that has the feel, drape characteristics, and other properties of typical fabrics used to produce garments and the like. Thus, the electrically conductive yarns can be incorporated into the fabric without undesirably increasing stiffness or imparting any other undesirable characteristics into the fabric.

In general, conductive yarns for use in fabrics of the present disclosure can be made from any suitable conductive material. The conductive material, for instance, may comprise a metal, a metallic compound, a conductive polymer, or mixtures thereof. The yarn can comprise a monofilament yarn, a multifilament yarn, and possibly a spun yarn. In one embodiment, for instance, the conductive yarns comprise monofilament yarns. The entire yarn can be made from a conductive material. Alternatively, the yarn may comprise a multicomponent yarn containing a conductive component and a non-conductive component. For instance, in one embodiment, the multicomponent yarn may comprise a bicomponent yarn in which the conductive component comprises the core surrounded by a non-conductive sheath. Alternatively, the conductive component may comprise the sheath while the non-conductive component may comprise the core. In still another embodiment, the conductive component and the non-conductive component can be in a side-by-side relationship within the yarn.

In one embodiment, the conductive yarn comprises a core-sheath type conductive fiber, such as a monofilament fiber containing a core made from a conductive polymer. For instance, the conductive polymer used to make the core may comprise an acetylene conductive polymer, a pyrrole conductive polymer, a thiophene-based conductive polymer, a phenylene conductive polymer, an aniline conductive polymer, or the like.

For example, the conductive portion of the fiber may comprise an acetylene-based, 5-membered heterocyclic system. Monomers that may be used to produce the conductive polymer include, for instance, 3-methylpyrrole, 3-ethylpyrrole, 3-dodecylpyrrole 3-alkylpyrrole, 3,4-dimethylpyrrole, 3-methyl-4-3,4-dialkylpyrrole, dodecylpyrrole, N-methylpyrrole, N-alkylpyrrole such as N-dodecylpyrrole, N-methyl-3-methylpyrrole, N-alkyl-3-alkylpyrrole such as N-ethyl-3-dodecylpyrrole, 3-carboxymethylpyrrole, and the like. In an alternative embodiment, the conductive polymer may comprise a thiophene-based polymer such as an isothianaphthene-based polymer. Other examples of thiophene-based conductive polymers include poly-3,4-ethylene dioxythiophene. An example of a phenylene conductive polymer is poly-p-phenylene vinylene. The above polymers can also be mixed together in forming the conductive portion of a yarn.

In one embodiment, a dopant may be added to the conductive polymer in order to improve conductivity. The dopant, for instance, may comprise a halide ion, such as a chloride ion, or a bromide ion. Other dopants include perchlorate ions, tetrafluoroborate ions, hexafluoroarsenate ions, sulfate ions, nitrate ions, thiocyanate ions, hexafluoride silicic acid ions, trifluoroacetate ions, phosphate ions, phenylphosphate ions, and the like. Particular examples of dopants include hexafluorophosphate ions, tosylate ions, ethylbenzene sulfonate ions, alkylbenzene sulfonate ions such as dodecylbenzene sulfonate ions, methylsulfonate ions, other alkyl sulfonate ions, polyacrylic acid ions, polyvinyl sulfonic acid ions, polystyrene sulfonate ions, poly(2-acrylamido-2-methylpropanesulfonic acid ions, and the like. The amount of dopant added to the conductive polymer can vary depending upon the particular application. For instance, the dopant can be combined with the conductive polymer in an amount from about 3% to about 50% by weight, such as from about 10% to about 30% by weight.

In one embodiment, a conductive portion of a multicomponent fiber can be formed by applying a metallic coating to a polymer resin. The polymer resin can comprise any of the conductive polymers described above or can comprise a non-conductive polymer. In an alternative embodiment, a conductive filler can be loaded into a thermoplastic resin. The thermoplastic resin can comprise a conductive polymer as described above or non-conductive polymer.

Metals well suited for coating a polymer material include gold, silver, chrome, iron, and the like. Conductive particles that may be used include any of the metals described above in addition to aluminum, graphite, other carbon particles, carbon fibers, carbon black, and the like.

In yet another embodiment, the conductive portion of the multicomponent fiber or filament may comprise a carbon filament.

In one particular embodiment, the electrically conductive composite fiber of the present disclosure includes a conductive polymer layer made of a thermoplastic polyamide containing from about 13% to about 60% by weight of an electrically conductive particulate matter, such as carbon black, graphite, boron nitride, or the like. The fiber further includes a non-conductive component made of a thermoplastic polyamide.

In another embodiment, the conductive yarn comprises a thermoplastic polymer covered with a metal, such as silver or stainless steel. The thermoplastic polymer may comprise, for instance, a polyamide such as nylon or a polyester.

Multicomponent fibers and yarns made in accordance with the present disclosure can include a non-conductive component in addition to a conductive component. The non-conductive component can be made from any suitable natural or synthetic polymer. For instance, the non-conductive portion can be made from a polyamide, such as nylon 6 or nylon 66. Alternatively, the non-conductive portion can comprise a polyester, such as polyethylene terephthalate, polybutylene terephthalate, copolymers thereof, and the like. In yet another embodiment, the non-conductive component may comprise a polyolefin, such as polyethylene or polypropylene including copolymers thereof. In yet another embodiment, the non-conductive portion may comprise a polyacrylonitrile or a polyvinyl alcohol polymer. The relative amounts of the conductive component in relation to the non-conductive component can vary widely depending upon various different factors. The amount of the conductive component, for instance, can depend on the conductivity of the material and the type of materials being used. In general, the conductive component can comprise from about 20% to about 90% of the multicomponent fiber, such as from about 30% to about 70% by weight.

In another embodiment of the present disclosure, the conductive yarn may comprise a multifilament yarn containing conductive filaments. For instance, a multifilament yarn can be formed in which one or more conductive filaments can be surrounded by non-conductive filaments. The non-conductive filaments can be made from any of the non-conductive thermoplastic polymers described above. The conductive filaments, on the other hand, can be made from any of the conductive materials described above including conductive polymers, a metallic material, and the like.

In yet another embodiment, a multifilament yarn made from thermoplastic filaments can be covered with carbon nanotube to render the yarn conductive.

The conductive yarns made in accordance with the present disclosure can be woven or knitted into any suitable fabric structure capable of carrying out the process of the present disclosure. As described above, the fabric structure can be made entirely from conductive yarns. Alternatively, the fabric can be made from a combination of conductive yarns and non-conductive yarns. For instance, the conductive yarns can be strategically placed within the fabric in order to form a countless variety of different electrical circuits for use in carrying out the processes of the present disclosure.

In one embodiment, the fabric structure of the present disclosure comprises a knitted fabric containing conductive yarns and non-conductive yarns. In general, any suitable knitting machine may be used in accordance with the present disclosure. For instance, the knitting machine may comprise a weft knitting machine, a warp knitting machine, or a seamless knitting machine. In one embodiment, for instance, a Santoni circular knitting machine is used. Knitting machines for use in the present disclosure offer various advantages and benefits. For instance, through the use of a knitting machine, a three-dimensional knitted architecture can be constructed that can advantageously place conductive yarns in needed locations. In addition, many knitting machines allow users to select needle-to-needle operations electronically and can have a variety of different yarn feeders.

In one embodiment, for instance, the fabric is formed or knitted on a circular knitting machine that has a computerized electronic needle and yarn feed selection system. Typically cylindrical blanks are knitted using both the cylindrical needles and the dial needles. The cylinder needles knit a first series of courses and the dial needles can knit a second series of courses.

Alternatively, the knitting machine can include more than two courses. For instance, the knitting machine can include from about two to about sixteen courses, such as from about six to about twelve courses.

In one embodiment, a knitting machine can be used with eight feeders. A fabric can be made having a three-dimensional configuration from the knitting machine. For instance, a double-faced fabric can be produced. In this manner, the face of the fabric can include primarily only non-conductive yarns, while the back of the fabric can include conductive yarns. For instance, a plating technique can be used to produce the fabric. Plating is a knit construction in which two or more yarns are fed simultaneously. The second yarn is generally of a different type than the first yarn. During the knitting process, the second yarn is placed under the first yarn so that each yarn can be rolled to a specific side of the fabric. In this manner, one yarn can appear primarily on the face of the fabric and the other yarn can primarily appear on the back of the fabric.

In one embodiment, in addition to a non-conductive yarn and a conductive yarn, the fabric can include various other yarns. For instance, the fabric can include an elastic yarn that when stretched recovers. For instance, the elastic yarn may comprise Spandex.

In one embodiment, for instance, the knitted yarn may be formed from about four to about six courses. The first course, for instance, can be made from a non-conductive yarn, such as polyester, cotton, nylon, an acrylic polymer, or the like. The remaining courses, on the other hand, can comprise a single yarn or a combination of yarns. For instance, one of the courses can contain a conductive yarn in conjunction with a spandex yarn. A third course, on the other hand, may contain a non-conductive yarn in combination with a spandex yarn. A fourth course, on the other hand, may be made exclusively from the conductive yarn. All different combinations can be used and all different numbers of courses can be used to form the fabric. In this manner, a three-dimensional fabric architecture can be constructed particularly well suited for constructing electric circuits within the fabric and for the fabric to carry out the commands that are user inputted. During knitting, float loops can be used in order to obtain the desired construction.

In implementations wherein the interactive device 102 and/or the interactive device 104 are smart garments constructed in a suitable manner as described above, the smart garments can be configured to perform suitable functionality in accordance with example aspects of the present disclosure. For instance, the smart garment can be configured to detect input gestures performed by a user with respect to the smart garment. For instance, the user may perform a suitable touch gesture, hand gesture, etc. on a surface of the smart garment. The electrically conductive fibers of the smart garment can facilitate a detection of the input gesture by the input gesture detector associated with the interactive device. In this manner, the detection sensor(s) 114 can be electrically coupled to one or more of the electrically conductive fibers of the smart garment to form one or more electrical circuits configured to detect the input gesture as performed with respect to the smart garment.

Similarly, the one or haptic feedback devices 116 can further be implemented within the smart garment, and can be configured to provide suitable emotive contextual signals to the user in accordance with example aspects of the present disclosure. In some implementations, the haptic feedback device(s) implemented within the smart garment can include one or more actuators, engines, motors, etc. configured to provide the emotive contextual signals. In such implementations, the haptic feedback device(s) 116 can be electrically coupled to one or more electrically conductive fibers of the smart garment. In some implementations, the haptic feedback device(s) 116 can be one or more yarns of the smart garment. Such yarns of the smart garment can be configured to provide emotive contextual signals in accordance with example aspects of the present disclosure. For instance, the yarns can be configured to apply heat to the user through one or more electrical circuits formed by the yarns. As another example, the yarns can be configured to actuate to change the form of the smart garment. For instance, the yarns can be configured to actuate to tighten or loosen the smart garment around a wearer of the smart garment to provide a suitable mediated interaction.

Further still, the smart garment can be configured to monitor one or more biometric characteristics of the user, for instance, using the one or more biometric monitors 118 implemented within or with respect to the smart garment. In this manner, such biometric monitors 118 can be electrically coupled to one or more electrically conducting yarns of the smart garment to form one or more suitable circuits for monitoring suitable biometric characteristics of a wearer of the smart garment.

It will be appreciated that various suitable smart garments can be used in accordance with example aspects of the present disclosure. Such smart garments can be associated with one or more computing devices, sensors, feedback devices, etc. used to carry out example aspects of the present disclosure. In this manner, the smart garments constructed according to example aspects of the present disclosure, in association with a suitable computing device (e.g. having a suitable processor(s), memory device(s), etc. can be configured to be worn by a user, and to implement functionality of the present disclosure.

Figure 2:
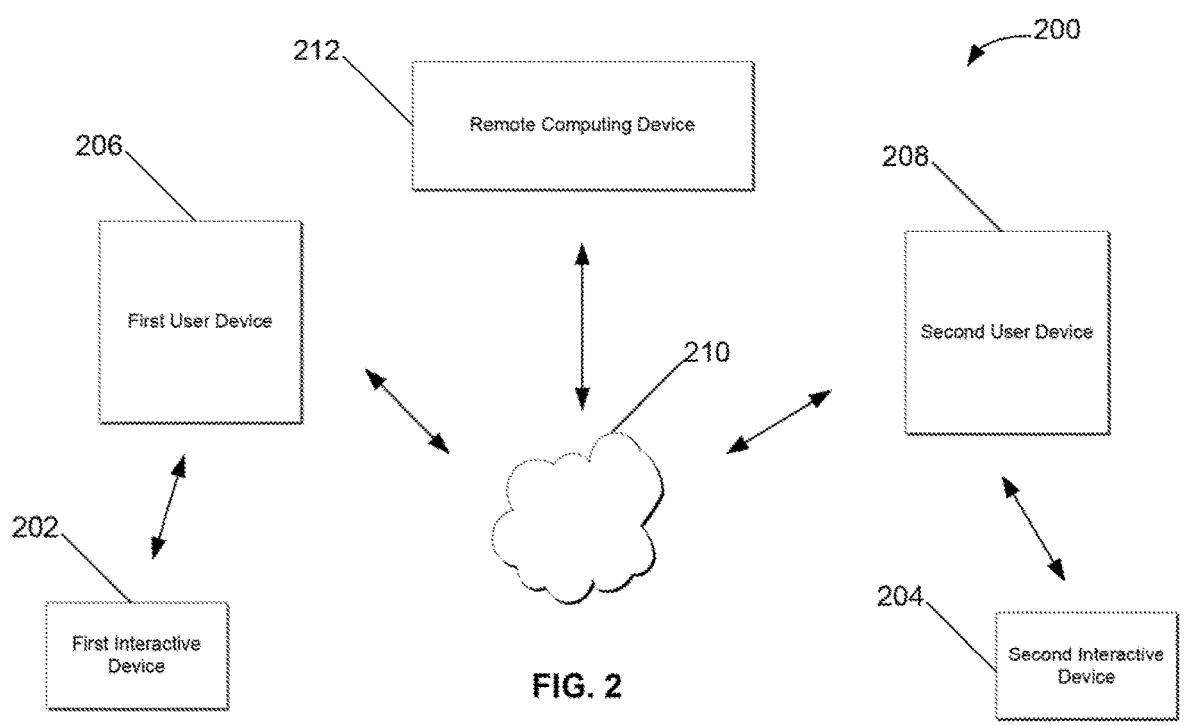
FIG. 2 depicts an example system for providing emotive contextual signals according to example embodiments of the present disclosure.

FIG. 2 depicts an example configuration of a system 200 for providing emotive contextual signals. The system 200 includes a first interactive device 202 and a second interactive device 204. In some implementations, the first interactive device 202 and the second interactive device 204 can respectively correspond to the first interactive device 102 and the second interactive device 104 depicted in FIG. 1. The first interactive device 202 can be communicatively coupled to a first user device 206, and the second interactive device 204 can be communicatively coupled to a second user device 208. For instance, the first interactive device 202 can be coupled to the first user device 206 via a network such as a Bluetooth network, Wi-Fi Direct network or other suitable network. Similarly, the second interactive device 204 can be communicatively coupled to a second user device 208 via a network such as a Bluetooth network, Wi-Fi Direct network or other suitable network.

Communication between the first interactive device 202 and the second interactive device 204 can be facilitated via the first user device 206 and the second user device 208. For instance, the first user device 206 and the second user device 208 can relay data communicated between the first interactive device 202 and the second interactive device 204. The first user device 206 and the second user device 208 can communicate via a network 210 (e.g. the Internet). In this manner the first interactive device 202 can provide data to the first user device 206. The first user device 206 can provide the data to the second user device 208 via the network 210. The second user device 208 can provide the data to the second interactive device 204.

In some implementations, the first user device 206 and/or the second user device 208 can communicate with a remote computing device 212, for instance, via the network 210. The remote computing device 212 can be a server, such as a web server. One or more example aspects of the present disclosure can be performed by the remote computing device 212. For instance, the signal determiner 108 and/or the signal determiner 112 can be implemented in the remote computing device 212. In this manner, data indicative of an input gesture performed by a user can be provided to the remote computing device 212 (e.g. from the first interactive device 202 or the second interactive device 204), and the signal determiner(s), as implemented in the remote computing device 212 can determine one or more emotive contextual signals to be provided to the first interactive device 202 and/or the second interactive device 204 in accordance with example aspects of the present disclosure.

In some implementations, the first user device 206 and the second user device 208 can facilitate a registration or pairing between the first interactive device 202 and the second interactive device 204. For instance, a first user associated with the first interactive device 202 can interact with the first user device 206 to establish communications between the first user device 206 and the first interactive device 202, as well as to establish communications between the first interactive device 202 and the second interactive device 204. Similarly, a second user associated with the second interactive device 204 can interact with the second user device 208 to establish communications between the second user device 208 and the second interactive device 204, as well as to establish communications between the second interactive device 204 and the first interactive device 202. In this manner the first user can establish a mediated social interaction with the second user, or vice versa.

It will be appreciated that the systems 100 and 200 depicted in FIGS. 1 and 2 respectively are depicted for illustrative purposes. Further, it will be appreciated that any suitable system configuration can be used to implement the example aspects of the present disclosure. For instance, the first interactive device 202 may communicate directly with the second interactive device 204. As another example, one or more example aspects of the present disclosure can be performed by the first user device 206 and/or the second user device 206. In some implementations, mediated social interactions can be established between more than two interactive devices. For instance, one or more additional interactive devices associated with one or more additional users can be included in the system. The one or more additional interactive devices can be configured to communicate with the first interactive device 202 and/or the second interactive device 204 via the network 210 and/or one or more additional user devices respectively associated with the one or more additional interactive devices. In this manner, mediated social interactions can be established between any suitable number of users.

Figure 3:
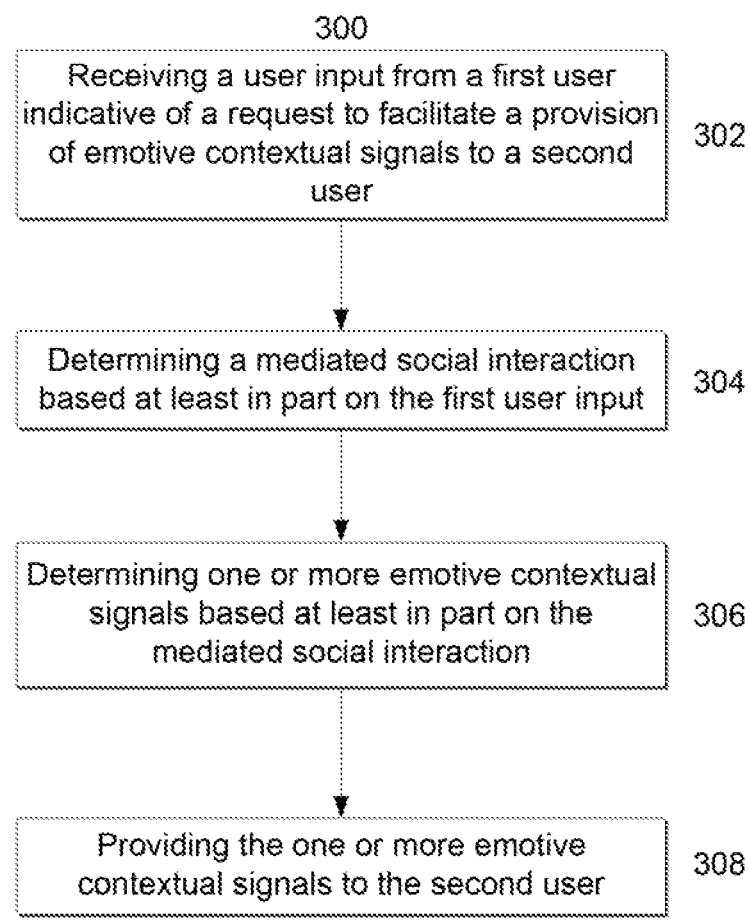
FIG. 3 depicts an example method of providing emotive contextual signals according to example embodiments of the present disclosure.

FIG. 3 depicts a flow diagram of an example method (300) of providing emotive contextual signals. The Method (300) can be implemented by one or more computing devices, such as one or more of the computing devices depicted in FIG. 5. In particular implementations, the method (300) can be implemented by the input gesture detector 106 and the signal determiner 108 depicted in FIG. 1. In addition, FIG. 3 depicts steps performed in a particular order for purposes of illustration and discussion. Those of ordinary skill in the art, using the disclosures provided herein, will understand that the steps of any of the methods discussed herein can be adapted, rearranged, expanded, omitted, or modified in various ways without deviating from the scope of the present disclosure.

At (302), the method (300) can include receiving a user input from a first user. The user input can be an input gesture indicative of a request to facilitate a provision of emotive contextual signals to a second user. For instance, the input gesture can be any suitable input gesture, such as a hand gesture, a touch gesture, a motion gesture, an application of pressure, an input using one or more suitable input devices (e.g. keyboard, mouse, trackpad, etc.), or other suitable input gesture. The input gesture can be performed with respect to a first interactive device associated with the first user. The first interactive device can be any suitable computing device capable of implementing example aspects of the present disclosure. In this manner, the first interactive device can be any suitable computing device configured to provide emotive contextual signals to a user in accordance with example aspects of the present disclosure. For instance the first interactive device can be a general purpose computer, special purpose computer, laptop, desktop, mobile device, navigation system, smartphone, tablet, wearable computing device (e.g. smart garment, fitness band, smart watch, etc.), a display with one or more processors, or other suitable computing device At (304), the method (300) can include determining a mediated social interaction based at least in part on the user input. The mediated social interaction can be determined based at least in part on the user input. For instance, the mediated social interaction can be mapped to the input gesture as part of a gesture mapping scheme that corresponds a plurality of suitable input gestures to a plurality of mediated social interactions and/or emotive contextual signals. For instance, the gesture mapping scheme can be specified within a lookup table or other suitable data structure. In this manner, determining the mediated social interaction can include accessing the gesture mapping scheme.

The mediated social interaction can be any suitable mediated social interaction, such as a mediated physical interaction. The mediated social interaction can be associated with an evocation of an emotional or biometric response within a user. For instance, the mediated social interaction can be associated with an evocation of a feeling of warmth, a calming or soothing feeling, a feeling of connectedness, a feeling of intimacy, or other suitable emotion. In some implementations, the mediated social interaction can be associated with a simulation of a particular action or behavior. The mediated social interaction can be associated with a particular form of touch or contact. For instance, the mediated social interaction can be associated with a simulation of holding hands, hugging, breathing, or other suitable behavior or action.

At (306), the method (300) can include determining one or more emotive contextual signals based at least in part on the mediated social interaction. For instance, the emotive contextual signals can be determined such that an application of the emotive contextual signals will bring about the desired mediated social interaction. For instance, the emotive contextual signals can attempt to simulate a particular behavior or action associated with the mediated social interaction. The emotive contextual signals can further attempt to stimulate an emotional or biometric response associated with the mediated social interaction.

The emotive contextual signals can be haptic feedback signals. For instance, such haptic feedback signals can include vibration, pressure, temperature (e.g. heat or warmth), electrical currents, forces, stress, strain, impacts, and/or other suitable forms of haptic feedback to be applied to the second user. It will be appreciated that the emotive contextual signals can be any other suitable forms of physical stimulation. In this manner, the emotive contextual signals can include any suitable combination of haptic feedback signals or other physical stimulations to achieve the desired mediated social interaction. As will be described in more detail below with regard to FIG. 4, in some implementations, the emotive contextual signals can be determined based at least in part on one or more biometric signals (e.g. heart rate, skin conductance, body temperature, etc.) associated with the second user. In this manner, the emotive contextual signals can be personalized for the user to establish the mediated social interaction based at least in part on the user's biometric characteristics.

In implementations wherein the interactive device is a smart garment according to example aspects of the present disclosure, the emotive contextual signals can include one or more signals provided by the smart garment. For instance, such signals can be provided by one or more actuators, motors, vibration engines, etc. electrically coupled to one or more conductive yarns of the smart garment. In some implementations, one or more yarns of the smart garment can be configured to provide emotive contextual signals. For instance, such one or more yarns can be configured to implement a circuit to provide heat to a wearer of the smart garment. As another example, such yarns can be implemented within a circuit to cause the yarns to actuate or compress, such that a fit of the smart garment with respect to the user can be adjusted (e.g. tightened or loosened).

In some implementations, one or more emotive contextual signals can further be determined for the first user. For instance, in instances wherein the mediated social interaction includes two-way contact, such as holding hands or hugging, the emotive contextual signals associated with such two-way contact can be determined for each user. In this manner, the emotive contextual signals can be applied to each user, such that each user experiences the mediated social interaction. In such implementations, the emotive contextual signals determined for the first user can be determined based at least in part on one or more biometric signals associated with the first user.

At (308), the method (300) can include providing the one or more emotive contextual signals to the second user. For instance, the one or more emotive contextual signals can be provided to the second user using one or more haptic feedback devices associated with an interactive device. Such haptic feedback devices can include one or more actuators, motors, vibration engines, electrically conductive yarns associated with a smart garment etc. The emotive contextual signals can be applied to the second user while the second user is making physical contact with the interactive device associated with the second user. In this manner, the emotive contextual signals can be applied to the skin of the second user.

Figure 4:
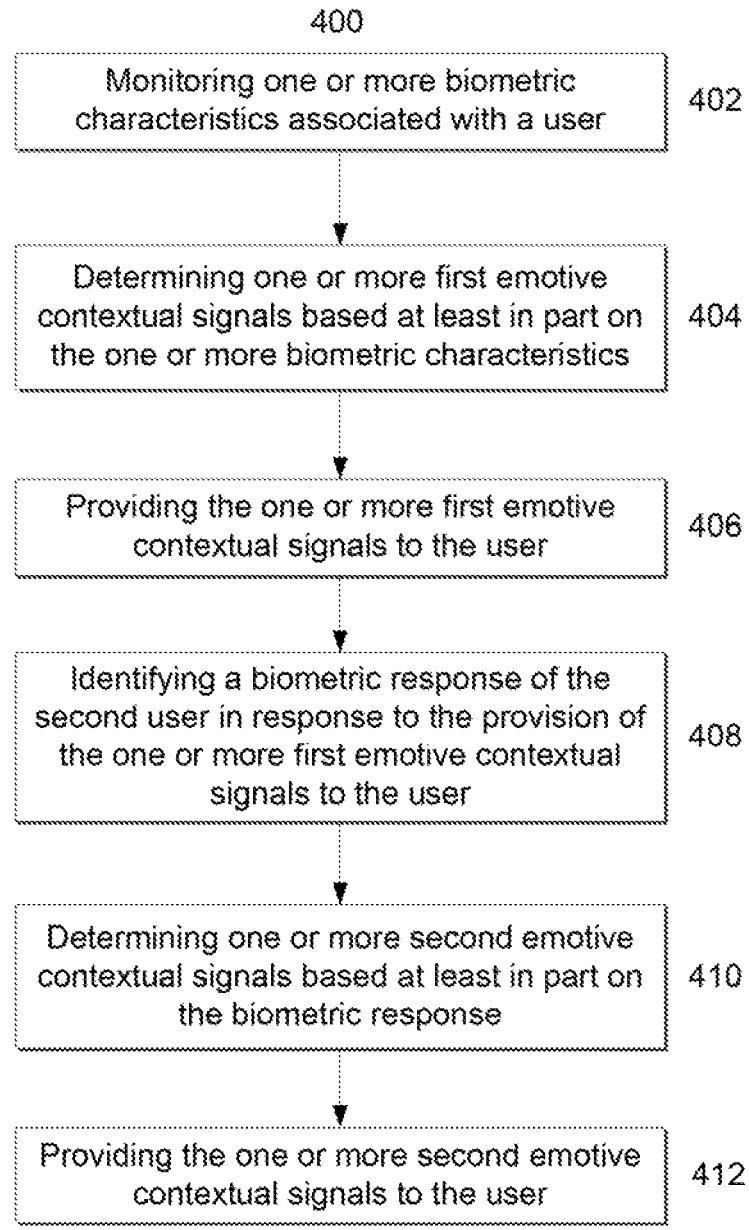
FIG. 4 depicts an example method of determining emotive contextual signals according to example embodiments of the present disclosure.

FIG. 4 depicts a flow diagram of an example method (400) of determining emotive contextual signals according to example embodiments of the present disclosure. The Method (400) can be implemented by one or more computing devices, such as one or more of the computing devices depicted in FIG. 5. In particular implementations, the method (400) can be implemented by the input gesture detector 106 and the signal determiner 108 depicted in FIG. 1. In addition, FIG. 4 depicts steps performed in a particular order for purposes of illustration and discussion.

At (402), the method (400) can include monitoring one or more biometric characteristics associated with a user. The user can be a user to which emotive contextual signals are to be applied. For instance, the user can be the second user described with regard to FIG. 3. The one or more biometric characteristics can be associated with biometric signals of the user, such as heart rate, body temperature, skin conductance, or other suitable biometric signal. The biometric characteristics can be monitored by an interactive device associated with the user. For instance, the interactive device can monitor the biometric characteristics using one or more biometric monitors while the user is making contact with the interactive device.

At (404), the method (400) can include determining one or more first emotive contextual signals based at least in part on the one or more biometric characteristics. For instance, the emotive contextual signals can include one or more haptic feedback signals or other physical stimulations designed to implement a mediated social interaction between the user and one or more additional users. For instance, particular biometric characteristics respond differently to different emotive contextual signals. In this manner, the emotive contextual signals determined to establish a particular mediated social interaction can vary based on the biometric characteristics of the user to whom the emotive contextual signals are to be applied.

In some implementations, the mediated social interaction can be designed to evoke a particular biometric response from the user or to bring the biometric characteristics of the user to a particular state or provide a target response. In this manner, the monitored biometric characteristics can be used to determine the emotive contextual signals that can be used to achieve such goals.

At (406), the method (400) can include providing the one or more first emotive contextual signals to the user. For instance, the first emotive signals can be provided to the user via one or more haptic feedback devices associated with the interactive device.

At (408), the method (400) can include identifying a biometric response of the second user that occurs in response to the provision of the one or more first emotive contextual signals to the user. For instance, the biometric characteristics of the user can change in response to receiving the emotive contextual signals. In this manner, identifying the biometric response can include comparing the biometric characteristics of the user at a first point in time prior to the provision of the emotive contextual signals to the biometric characteristics of the user at a second point in time subsequent to the provision of the emotive contextual signals. The biometric response can correspond to the change in the biometric characteristics of the user at the second time relative to the first time.

At (410), the method (400) can include determining one or more second emotive contextual signals to be provided to the user based at least in part on the biometric response. The second emotive contextual signals can include one or more different haptic feedback signals or one or more different haptic feedback signal combinations relative to the first emotive contextual signals. For instance, the emotive contextual signals can evoke an unintended biometric and/or emotional response in the user. In such instances, the emotive contextual signals can be adjusted to correct such unintended response(s). In this manner, the emotive contextual signals can be adjusted to more accurately facilitate the intended effects of the intended mediated social interaction.

In some implementations, the biometric response of the user can be used to "learn" personalized emotive contextual signals that are better tailored for the user. For instance, the biometric responses of the user can be analyzed with respect to a plurality of emotive contextual signals provided to the user over time to learn how the user responds to the emotive contextual signals. Such learning techniques can be used to predict a user response to future provisions of emotive contextual signals. In this manner, various emotive contextual signals or emotive contextual signal combinations can be mapped to various mediated social interactions based on the tracked user responses to such emotive contextual signals. In some implementations, such learning and/or mapping techniques can be implemented using machine learning techniques. For instance, a suitable machine learning model (e.g. neural network or other suitable model) can be trained based on the user's biometric responses, and can be used to determine emotive contextual signals to be provided to the user for various mediated social interactions.

At (412), the method (400) can include providing the one or more second emotive contextual signals to the user. For instance, the emotive contextual signals can be provided to the user via the one or more haptic feedback devices associated with the interactive device of the user.

Figure 5:
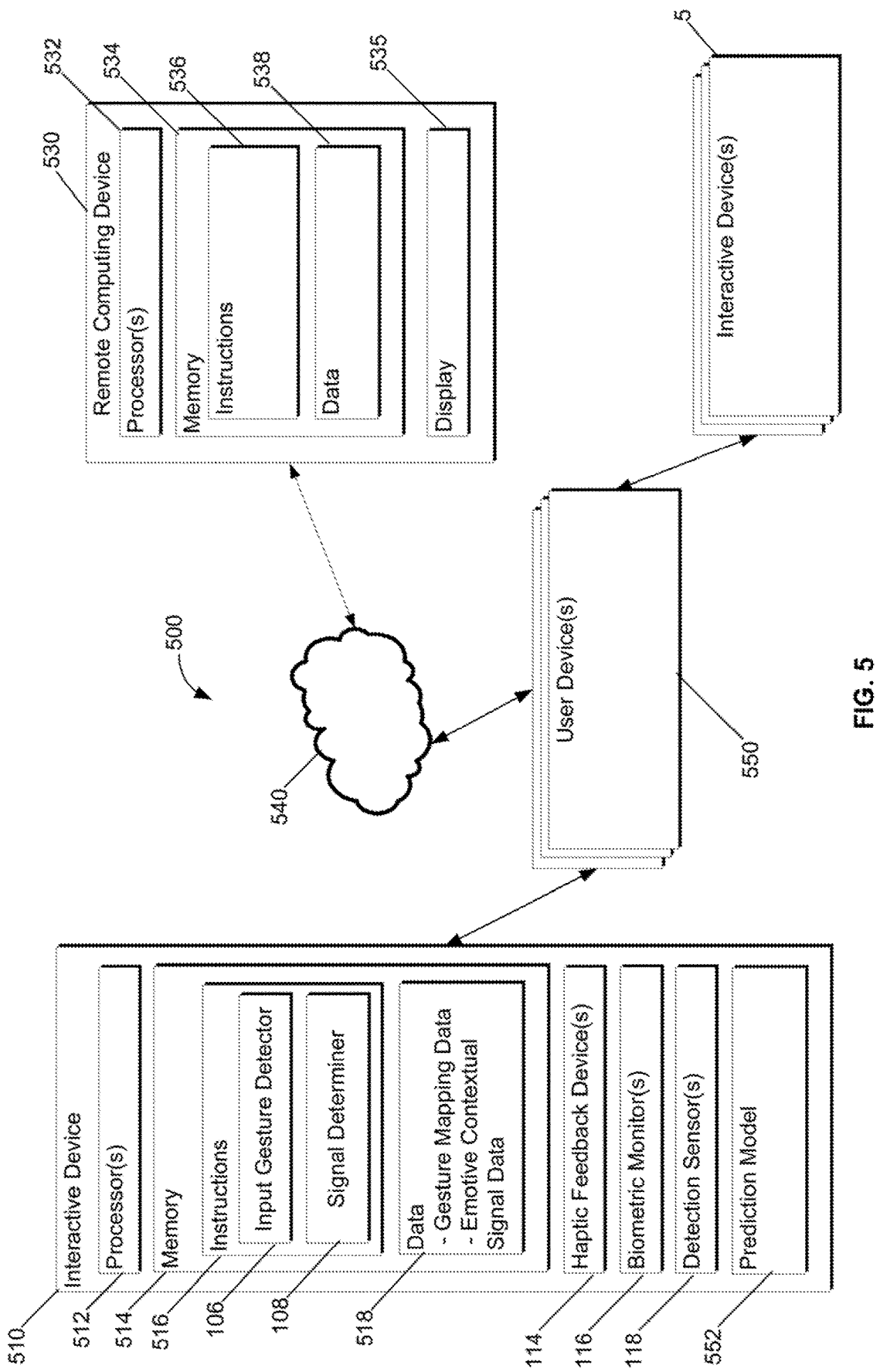
FIG. 5 depicts an example system according to example embodiments of the present disclosure.

FIG. 5 depicts an example computing system 500 that can be used to implement the methods and systems according to example aspects of the present disclosure. The system 500 can be implemented using a client-server architecture that includes an interactive device 510 that communicates with one or more remote devices 530 over a network 540. The system 500 can be implemented using other suitable architectures.

The system 500 includes an interactive device 510, The interactive device 510 can be, or can be associated with, any suitable computing device, such as a general purpose computer, special purpose computer, laptop, desktop, mobile device, navigation system, smartphone, tablet, wearable computing device, a display with one or more processors, or other suitable computing device. In some implementations, the interactive device 510 can be a smart garment in accordance with example aspects of the present disclosure. The interactive device 510 can have one or more processors 512 and one or more memory devices 514. The interactive device 510 can also include a network interface. The network interface can be used to communicate with one or more user devices 550 over a network, such as a direct network (e.g. Bluetooth network, Wi-Fi direct network, etc.). In some implementations, the network interface can be used to communicate with one or more remote devices 530 over the network 540. The network interface can include any suitable components for interfacing with one more networks, including, for example, transmitters, receivers, ports, controllers, antennas, or other suitable components.

The one or more processors 512 can include any suitable processing device, such as a microprocessor, microcontroller, integrated circuit, logic device, graphics processing units (GPUs) dedicated to efficiently rendering images or performing other specialized calculations, and/or other suitable processing device. The one or more memory devices 514 can include one or more computer-readable media, including, but not limited to, non-transitory computer-readable media, RAM, ROM, hard drives, flash drives, or other memory devices. The one or more memory devices 514 can store information accessible by the one or more processors 512, including computer-readable instructions 516 that can be executed by the one or more processors 512. The instructions 516 can be any set of instructions that when executed by the one or more processors 512, cause the one or more processors 512 to perform operations. For instance, the instructions 516 can be executed by the one or more processors 512 to implement the input gesture detector 106 and the signal determiner 108 described with reference to FIG. 1.

As shown in FIG. 5, the one or more memory devices 514 can also store data 518 that can be retrieved, manipulated, created, or stored by the one or more processors 512. The data 518 can include, for instance, gesture mapping data, emotive contextual signals data generated according to example aspects of the present disclosure, and other data. The data 518 can be stored locally at the interactive device 510 and/or remote from the interactive device 510, such as in one or more databases. The one or more databases can be implemented within the server 530, or can be connected to the interactive device 510 by a high bandwidth LAN or WAN, or can also be connected to interactive device 510 through network 540. The one or more databases can be split up so that they are located in multiple locales.

The interactive device 510 can include various input/output devices for providing and receiving information from a user, such as a touch screen, touch pad, data entry keys, speakers, and/or a microphone suitable for voice recognition. For instance, the interactive device 510 can have a display device for presenting a user interface. The interactive device can further include one or more detection sensors 114 configured to detect an input gesture performed by a user in accordance with example aspects of the present disclosure, haptic feedback devices 116 configured to provide emotive contextual signals in accordance with example embodiments of the present disclosure, and one or more biometric monitors 118 configured to monitor one or more biometric characteristics of the user in accordance with example aspects of the present disclosure.

The interactive device can further include a prediction model 552. The prediction model 552 can be a suitable machine learning model configured to receive a mediated social interaction and/or one or more biometric characteristics of a user as input and to provide one or more emotive contextual signals corresponding to the mediated social interaction as output. In this manner, the prediction model 552 can predict one or more emotive contextual signals that will effectuate the selected mediated social interaction for the user. The prediction model 552 can be trained using suitable training data, and can be adjusted based at least in part on biometric responses of the user to various provisions of various emotive contextual signals over one or more periods of time. The prediction model can be trained by a training system configured to implement one or more suitable training techniques, such as, for example, backwards propagation of errors. The training system can be implemented, for instance, by the remote device 530, the user device 550, the interactive device 510, or in other suitable location. The prediction model can be used by the signal determiner 108 to determine suitable emotive contextual signals to be provided to a user. In some implementations, the prediction model 552 can be implemented at the remote computing device 530, the user device 550, or at other suitable locations.

The interactive device 510 can exchange data with one or more user devices 550 (e.g. over a direct network) and/or with one or more remote devices 530 over the network 540. For instance, a remote device can be a server, such as a web server. A user device can be any suitable user device, such as a smartphone, tablet, laptop, desktop, wearable computing device, etc. The system 500 can include any suitable number of interactive devices 510, user devices 550 and/or remote devices 530. The remote devices 530 can be connected to the interactive device 510 over the network 540.

Similar to the interactive device 510, a remote device 530 and/or a user device 550 can include one or more processor(s) 532 and a memory 534. The one or more processor(s) 532 can include one or more central processing units (CPUs), and/or other processing devices. The memory 534 can include one or more computer-readable media and can store information accessible by the one or more processors 532, including instructions 536 that can be executed by the one or more processors 532 and data 538.

In some implementations, one or more of the input gesture detector 106 or the signal determiner 108 can be implemented by a remote device 530 and/or a user device 550. In this manner, the functionality associated with the one or more of the input gesture detector 106 or the signal determiner 108 can be performed by a remote device 530 and/or a user device 550. For instance, the interactive device 510 can communicate with a remote device 530 and/or a user device 550 to implement example aspects of the present disclosure.

The remote device(s) 530 can also include a network interface used to communicate with one or more remote computing devices (e.g. interactive device 510) over the network 540. The network interface can include any suitable components for interfacing with one more networks, including for example, transmitters, receivers, ports, controllers, antennas, or other suitable components.

The network 540 can be any type of communications network, such as a local area network (e.g. intranet), wide area network (e.g. Internet), cellular network, or some combination thereof. The network 540 can also include a direct connection between a remote device 530 and the interactive device 510. In general, communication between the interactive device 510 and a remote device 530 can be carried via network interface using any type of wired and/or wireless connection, using a variety of communication protocols (e.g. TCP/IP, HTTP, SMTP, FTP), encodings or formats (e.g. HTML, XML), and/or protection schemes (e.g. VPN, secure HTTP, SSL).

The technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A computer-implemented method of providing emotive contextual signals to a user, the method comprising:

receiving, by a first computing device, a user input from a first user indicative of a request to facilitate a provision of emotive contextual signals to a second user;

determining, by a second computing device, one or more first emotive contextual signals to be provided to the second user based at least in part on the user input, the one or more first emotive contextual signals comprising one or more first haptic signals intended to facilitate a mediated social interaction associated with the second determining, by the second computing device, an emotional response of the second user to the one or more first emotive contextual signals; and comparing, by the second computing device, the determined emotional response of the second user to a target emotional response.

2. The computer-implemented method of claim 1, further comprising providing; by the second computing device, the one or more first emotive contextual signals to the second user.

3. The computer-implemented method of claim 1, wherein the user input comprises an input gesture performed by the first user with respect to the first computing device, the input gesture being associated with the mediated social interaction.

4. The computer-implemented method of claim 3, wherein the input gesture comprises a physical interaction by the first user with the first computing device.

5. The computer-implemented method of claim 3, wherein the first computing device comprises one or more gesture detection sensors, and wherein receiving the user input comprises detecting the input gesture via the one or more gesture detection sensors.

6. The computer-implemented method of claim 1, wherein the second computing device comprises one or more haptic devices and wherein determining one or more first emotive contextual signals comprises determining the one or more first haptic signals to be provided to the second user by the one or more haptic devices.

7. The computer-implemented method of claim 1, further comprising determining, by the second computing device, one or more second emotive contextual signals based at least in part on the comparison of the determined emotional response to the target emotional response.

8. The computer-implemented method of claim 1, wherein determining, by the second computing device, an emotional response of the second user to the one or more first emotive contextual signals comprises measuring, by the second computing device, one or more biometric signals associated with the second user.

9. The computer-implemented method of claim 8, wherein the one or more biometric signals comprise one or more of a heart rate associated with the second user, a temperature associated with the second user, or a skin conductance associated with the second user.

10. The computer-implemented method of claim 1, wherein the first and second computing devices are associated with smart garments having a plurality of electrically conductive yarns configured to implement one or more circuits.

11. The computer-implemented method of claim 1, wherein determining, by a second computing device, one or more first emotive contextual signals comprises determining the one or more first emotive contextual signals using one or more machine learning techniques.

12. The computer-implemented method of claim 1, wherein determining, by the second computing device, one or more first emotive contextual signals to be provided to the second user comprises determining the one or more first emotive contextual signals based at least in part on one or more characteristics of the second user.

13. A computing system, comprising:

one or more processors; and one or more memory devices, the one or more memory devices storing compute readable instructions that when executed by the one or more processors cause the one or more processors to perform operations, the operations comprising:

receiving a user input from a first user indicative of a request to facilitate a provision of emotive contextual signals to a second user;

determining one or more first emotive contextual signals to be provided to the second user based at least in part on the user input, the one or more first emotive contextual signals comprising one or more first haptic signals intended to facilitate a mediated social interaction associated with the second user;

determining an emotional response of the second user to the one or more first emotive contextual signals; and comparing the determined emotional response of the second user to a target emotional response.

14. The computing system of claim 13, further comprising one or more haptic devices, and wherein the operations further comprise providing the one or more first emotive contextual signals to the second user via the one or more haptic devices.

15. The computing system of claim 13, the operations further comprising determining one or more second emotive contextual signals based at least in part on the comparison of the determined emotional response to the target emotional response.

16. One or more tangible, non-transitory computer-readable media storing computer-readable instructions that when executed by one or more processors cause the one or more processors to perform operations, the operations comprising:

receiving a user input from a first user indicative of a request to facilitate a provision of emotive contextual signals to a second user; and determining one or more first emotive contextual signals to be provided to the second user based at least in part on the user input and one or more characteristics of the second user, the one or more first emotive contextual signals comprising one or more first haptic signals intended to facilitate a mediated social interaction associated with the second user.

17. The one or more tangible, non-transitory computer-readable media of claim 16, wherein the user input comprises an input gesture performed by the first user with respect to the first computing device, the input gesture being associated with the first emotional response.

18. The one or more tangible, non-transitory computer-readable media of claim 16, wherein determining one or more first emotive contextual signals comprises determining the one or more first emotive contextual signals based at least in part on one or more biometric characteristics of the second user.

* * * * *